United States Patent [19]

Kanda

[11] Patent Number: 5,675,410
[45] Date of Patent: Oct. 7, 1997

[54] TABLET SAMPLE PREPARER FOR INFRARED SPECTROPHOTOMETER

[75] Inventor: Yasushi Kanda, Osaka, Japan

[73] Assignee: Chromato Science Co., Ltd., Osaka, Japan

[21] Appl. No.: 610,859

[22] Filed: Mar. 5, 1996

[51] Int. Cl.⁶ .................................................. G01N 21/01
[52] U.S. Cl. ........................................ 356/244; 356/36
[58] Field of Search ........................ 356/36, 244, 440

[56] References Cited

U.S. PATENT DOCUMENTS

| | | | |
|---|---|---|---|
| 3,829,216 | 8/1974 | Persidsky | 356/34 |
| 5,207,984 | 5/1993 | Kheiri | 356/244 |

FOREIGN PATENT DOCUMENTS

| | | | |
|---|---|---|---|
| 2257295 | 6/1991 | United Kingdom | 356/244 |

*Primary Examiner*—Frank G. Font
*Assistant Examiner*—Zandra V. Smith
*Attorney, Agent, or Firm*—Nikaido, Marmelstein, Murray & Oram LLP

[57] ABSTRACT

An annular frame body of lead is fixed to one surface of a substrate of copper, and a hole is provided in a portion of the substrate corresponding to the center of the frame body. The frame body is fixed to one end of the substrate, while the other end of the substrate is bent toward a side which is opposite to that provided with the frame body for defining an engage portion, so that the substrate engages with a sample holder of an FTIR to be stably mounted thereon. Sample mixture is charged inside the frame body and in the hole of the substrate, and pressurized and shaped with a press.

6 Claims, 4 Drawing Sheets

TABLET SAMPLE PREPARER FOR INFRARED SPECTROPHOTOMETER

BACKGROUND OF THE INVENTION

1. Field of the Invention

The present invention relates to a sample preparer for pressurizing a mixture of solid sample powder with powder of an infrared non-absorbent such as KBr using a press thereby making a tablet sample, in order to measure a solid sample in an infrared spectrophotometer such as an FTIR (Fourier transform infrared spectrophotometer).

2. Description of the Background Art

In order to measure a solid sample in an FTIR, 0. several % to several % of solid sample powder is mixed into KBr powder, and the mixture is pressurized to be shaped into a tablet. The shaped tablet sample is mounted on a sample chamber of the FTIR, to be subjected to measurement of infrared absorption by a transmission method.

The tablet sample is prepared by shaping mixed powder containing a sample into a disc. Mainly prepared are two types of tablet samples including a tablet sample having a diameter of 10 mm or 20 mm, and a small tablet called a microtablet having a diameter of several mm.

In order to shape a large-sized tablet, a tablet shaper shown in FIG. 1A is employed. This tablet shaper comprises a substrate 2 having a cylindrical projection 4 on a central portion of a disc, a cylindrical inner tube 6, having an inner diameter equal to the outer diameter of the projection 4, which is arranged on the substrate 2, and a mirror plate 8 having a mirror-polished surface which is stored in the inner tube 6, so that mixed powder (hereinafter referred to as sample mixture) 10 of sample powder and powder of an infrared non- absorbent such as KBr or the like is charged on the mirror-finished surface of the mirror plate 8. Another mirror plate 12 having a mirror-polished surface is further placed on the sample mixture 10 to face the mirror-finished surface to the sample mixture 10. An outer tube 14 is arranged to cover side and upper portions of the inner tube 6, and a push rod 16 which is positioned above the mirror plate 12 is arranged on a central portion of the outer tube 14. The push rod 16 is slidably fitted in the center of the outer tube 14, and an O-ring 18 for maintaining airtightness is provided between the push rod 16 and the outer tube 14. The substrate 2 is provided with an exhaust port 20 for discharging air from the sample mixture 10 through a vacuum pump.

Air is sucked and discharged from the sample mixture 10 which is held between the mirror plates 8 and 12 through the exhaust port 20, while the sample mixture 10 is pressurized from above by a press through the push rod 16, whereby a discoidal tablet having upper and lower surfaces which are parallel to each other is shaped.

FIG. 1B shows a shaper for shaping a microtablet. As shown in FIG. 1B, push plates 24 and 28 are fitted into a circular hole which is provided in the center of a cylindrical outer tube 22 from below and above respectively. The lower and upper push plates 24 and 28 are provided with cylindrical projections 26 and 30 having the same sizes as the hole of the outer tube 22 respectively. Forward ends of these projections 26 and 30 are worked into mirror-finished surfaces.

In order to shape a microtablet, the projection 26 of the lower push plate 24 is fitted in the hole of the outer tube 22 from below so that this projection 26 is charged with sample mixture 10 which is prepared by mixing sample powder with KBr powder in the hole of the outer tube 22, while the projection 30 of the push plate 28 is fitted into the hole from above. The lower push plate 24 is placed on a surface plate and the sample mixture 10 is pressurized by a press from above the upper push plate 28, to be shaped into a tablet.

The tablet shaped in FIG. 1A is taken out from the inner tube 6 and mounted on a sample holder of an FTIR, to be subjected to measurement. On the other hand, the tablet shaped by the shaper shown in FIG. 1B is mounted on a sample holder of an FTIR with the outer tube 22 in a state being stored in its hole, to be subjected to measurement.

While the press is selected from various ones such as a hydraulic press and a hand press, its pressure depends on the individual variation of the operator. Particularly in the case of a hand press, the pressure so remarkably depends on the individual variation of the operator that a tablet of stable quality cannot be readily obtained.

In the tablet shaper shown in FIG. 1A, it is necessary to wash and dry the inner tube 6 and the mirror plates 8 and 12 after shaping one sample, in order to shape a next sample. Also in the shaper shown in FIG. 1B, it is necessary to remove a measured tablet and wash and dry the outer tube 22, in order to shape a next sample tablet. KBr is so deliquescent that the portions such as the inner and outer tubes and the mirror plates which are brought into contact with the sample mixture must be completely dried for subsequent use. If the shaper is washed and dried upon shaping of every sample, however, the efficiency is deteriorated and the measurement time is disadvantageously increased in the case of measuring a number of solid samples. Further, the operation of washing and drying the shaper upon shaping of every sample is troublesome.

SUMMARY OF THE INVENTION

Accordingly, a first object of the present invention is to obtain a tablet having stable quality by suppressing influence by fluctuation of pressure resulting from the individual variation of the operator.

A second object of the present invention is to eliminate a troublesome operation of washing and drying a tablet shaper by charging sample mixture in a throwaway tablet sample preparer, pressurizing and shaping the same without employing a conventional tablet shaper.

A tablet sample preparer according to the present invention is formed by fixing an annular frame body consisting of a soft material to one surface of a hard substrate and providing a hole which is smaller than the inner size of a ring of the frame body in a substrate portion corresponding to a central portion of the ring, so that sample mixture is charged inside the frame body and in the hole of the substrate and pressurized for preparing a tablet sample.

The term "hard" for the hard substrate indicates that the substrate has such hardness that the substrate is hardly deformed by pressurization with a press for shaping a tablet, and a metal such as copper, brass or iron or resin generally called hard plastic belongs to such a hard material. On the other hand, the term "soft" for the soft material indicates that the material is readily deformed by the pressurization with the press for shaping the tablet, and a metal such as lead or resin generally called soft plastic belongs to the soft material.

When sample mixture is charged inside the frame body and in the hole of the substrate and pressurized with a press, the frame body consisting of the soft material is deformed to spread outwardly, thereby absorbing fluctuation in the pressure of the press. While the press may be selected from various ones such as a hydraulic press and a hand press, the individual variation of the operator is so extreme that the pressure fluctuates particularly in the case of a hand press, and hence the frame body absorbs the fluctuation of the pressure.

On the other hand, the hole of the hard substrate is not deformed. When an infrared spectroscopic analysis is made in a transmission type, infrared rays are transmitted through the hole of the substrate. Therefore, the shape of the tablet in the portion transmitting the infrared rays is stabilized.

Thus, the tolerance for pressure which can obtain a tablet of stable quality is increased due to the combination of the hole of the hard substrate having a stable shape and the frame body of the soft material absorbing the pressure.

The tablet sample which is prepared by the tablet sample preparer of the present invention is mounted on a sample chamber of an infrared spectrophotometer along with the substrate and the frame body, to be subjected to measurement. After the measurement, the substrate and the frame body are discarded along with the tablet sample, as a throwaway tablet sample preparer. The working efficiency is remarkably improved as compared with the prior art of washing and drying the preparer upon preparation of every tablet sample.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1A:
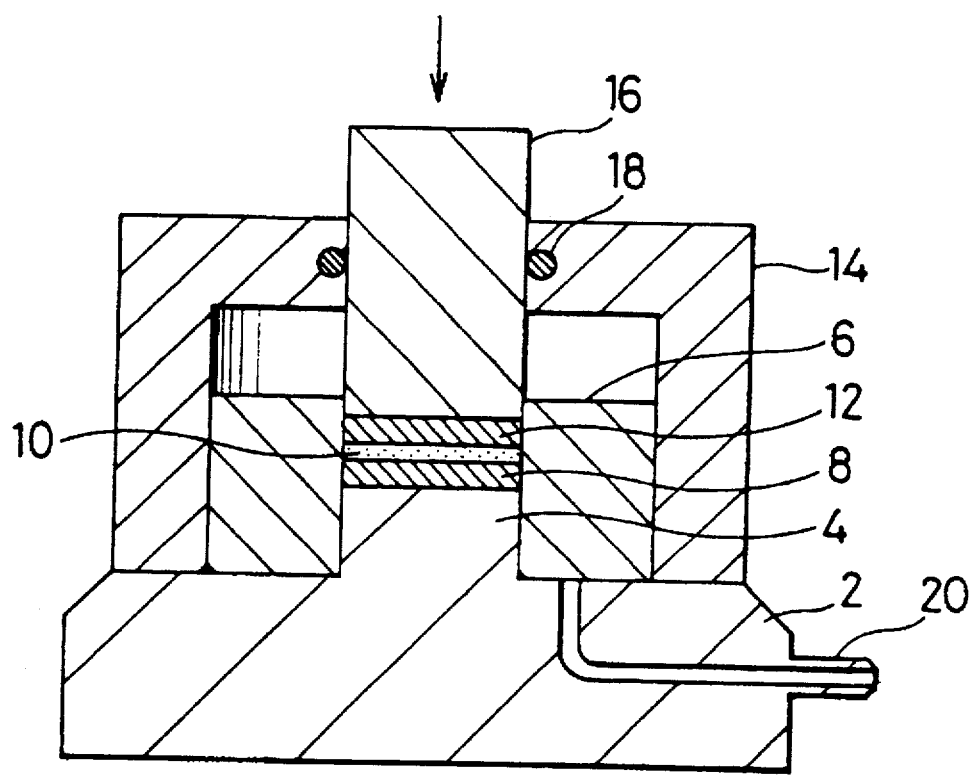
FIGS. 1A and 1B are longitudinal sectional views showing conventional tablet shapers respectively.
Figure 1B:
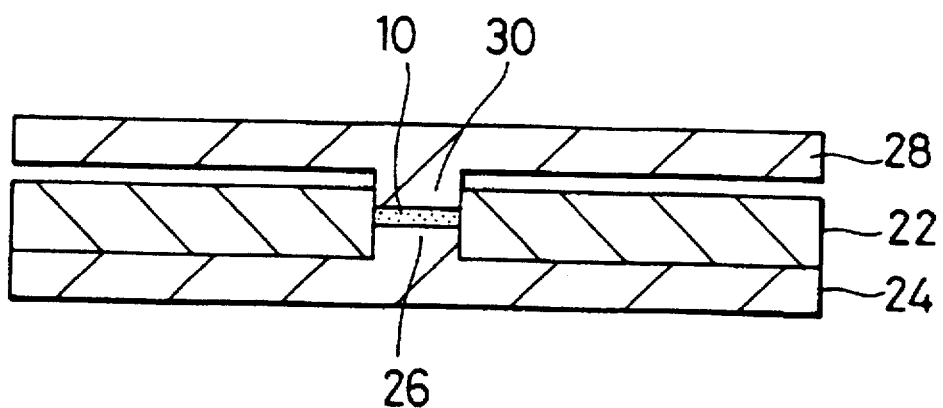
Figure 2A:
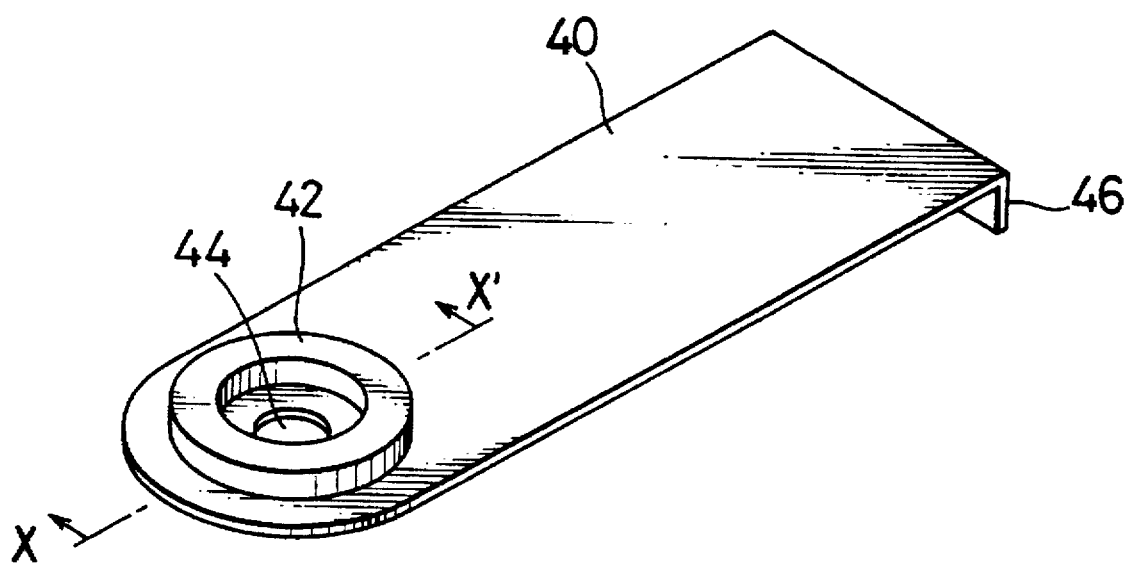
FIG. 2A is a perspective view showing an embodiment of the present invention.
Figure 2B:
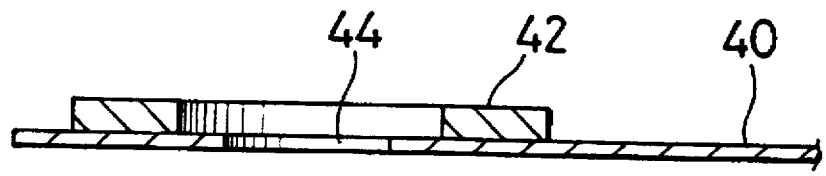
FIG. 2B is an enlarged sectional view taken along the line X—X in FIG. 2A.

Referring to FIGS. 2A and 2B showing an embodiment, an annular frame body 42 of lead is fixed to one surface of a substrate 40 of copper. A hole 44 which is equal to or smaller than the inner diameter of a ring of the frame body 42 is provided in a portion of the substrate 40 corresponding to the central portion of the frame body 42. For example, the substrate 40 is 0.2 mm in thickness, the frame body 42 is 0.5 mm in thickness, and the ring of the frame body 42 is 9 mm in outer diameter and 5 mm in inner diameter. Further, the hole 44 provided in the substrate 40 at the center of the frame body 42 is 3 mm in diameter, for example. The frame body 42 is fixed to one end of the substrate 40, while another end of the substrate 40 is bent by about 3 mm toward a side opposite to that provided with the frame body 42, thereby defining an engage portion 46.

The frame body 42 can be fixed onto the substrate 40 by soldering or spot welding.

With reference to FIGS. 3A, 3B, 4A and 4B, methods of preparing tablet samples with this tablet sample preparer are now described.

Figure 3A:
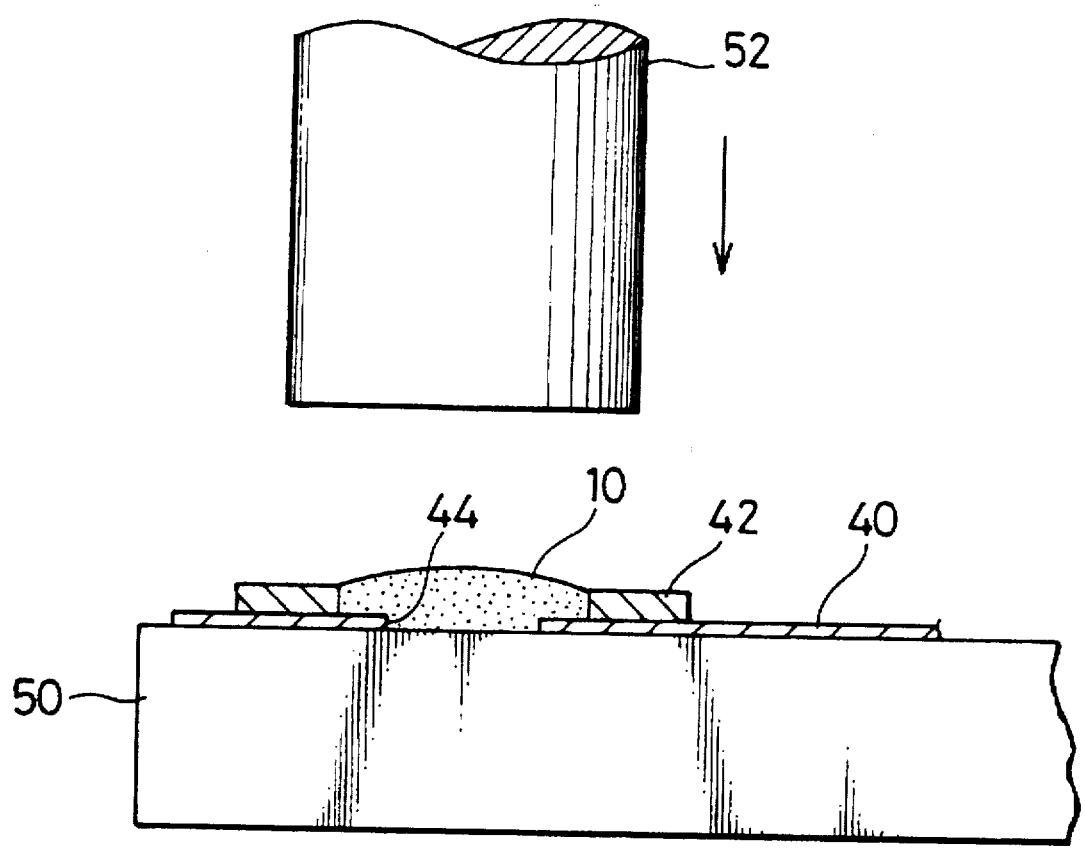
FIGS. 3A and 3B are sectional views showing steps of a tablet shaping method according to the embodiment.
Figure 3B:
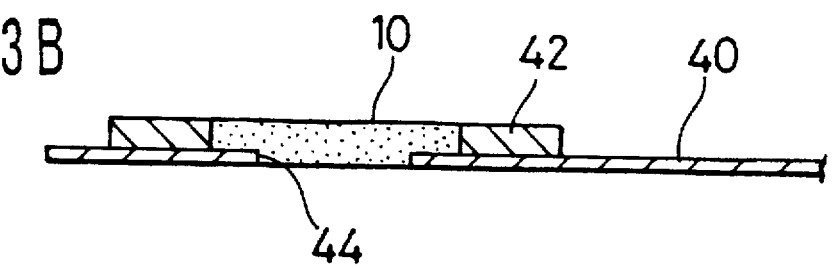

In the method of FIGS. 3A and 3B, the substrate 40 is placed on a surface plate 50 having a flat surface to face the surface not provided with frame body 42 thereto, so that sample mixture 10 is charged inside the frame body 42 and in the hole 44 of the substrate 40, as shown in FIG. 3A.

The sample mixture 10 is pressurized with a push rod 52 of a press from above. Thus, the sample mixture 10 is shaped in the frame body 42 and the hole 44 of the substrate 40 into a tablet sample, as shown in FIG. 3B. At this time, the frame body 42 of lead is deformed to spread outwardly, thereby absorbing fluctuation of the pressure of the press. Both upper and lower surfaces of the shaped tablet are flat.

Figure 4A:
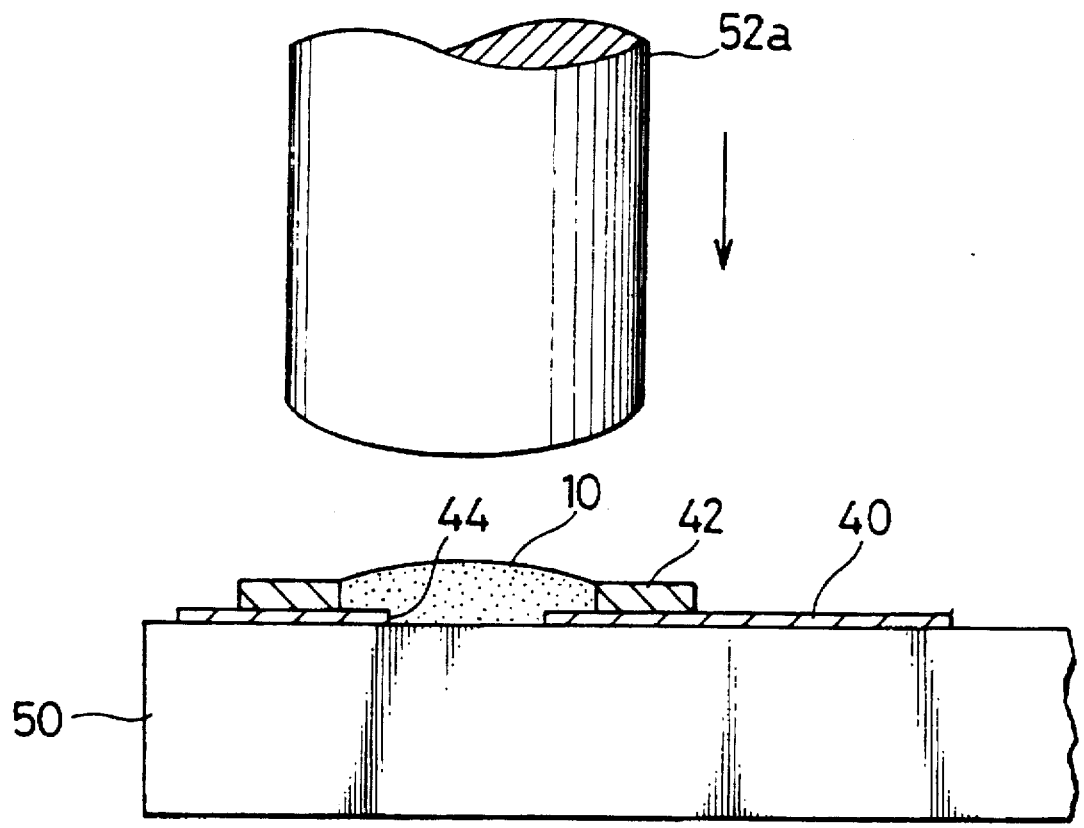
FIGS. 4A and 4B are sectional views showing steps of another tablet shaping method with an improved press according to the embodiment.
Figure 4B:
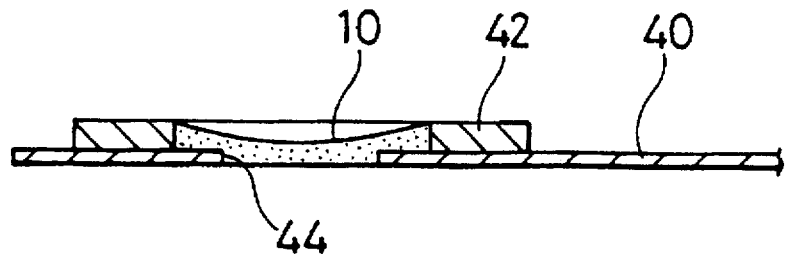

On the other hand, the method shown in FIGS. 4A and 4B is different from that of FIGS. 3A and 3B in a point that a forward end surface of a push rod 52a is convexly bent. When sample mixture 10 is pressed with the push rod 52a having such a convex bent surface, the shaped tablet has a flat lower surface along a flat surface of a surface plate 50, while its upper surface is concavely bent along the bent press surface of the push rod 52a, as shown in FIG. 4B.

While the inventor has separately proposed the method of bending the press surface of the push rod 52a, interference by infrared rays which are transmitted through the hole 44 or reflected by the upper and lower surfaces of the portion of the hole 44 is advantageously suppressed due to the antiparallel upper and lower surfaces of the shaped tablet, whereby the S-N ratio of the infrared absorption spectrum is improved. Due to the convex bending of the push rod 52a, further, force is concentrated to the central portion of the tablet which contributes to measurement and the pressure at the central portion is increased to transparentize KBr, whereby a tablet sample of high quality can be prepared.

While the substrate 40 is made of copper in the embodiment, the substrate 40 may alternatively be made of another hard metal such as brass or iron. While the frame body 42 is made of lead, further, the frame body 42 may alternatively be made of another soft material such as soft resin.

The tablet sample which is shaped by pressurization in the frame body 42 and the hole 44 of the substrate 40 is mounted on a sample holder of an FTIR along with the tablet sample preparer, to be subjected to measurement of infrared absorption. After the measurement, the tablet sample preparer may be discarded along with the tablet sample, and is not washed for re-employment, dissimilarly to the conventional tablet shaper.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A tablet sample preparer being formed by fixing an annular frame body consisting of a soft material to one surface of a hard substrate and providing a hole being smaller than the inner size of a ring of said frame body in a portion of said substrate corresponding to a central portion of said ring, for preparing a tablet sample by charging sample mixture being obtained by mixing powder of an infrared nonabsorbent with solid sample powder inside said frame body and in said hole and pressurizing said sample mixture.

2. The tablet sample preparer in accordance with claim 1, wherein said substrate is made of a metal or hard plastic, and said annular frame body is made of lead or soft plastic.

3. The tablet sample preparer in accordance with claim 2, wherein said substrate is made of a metal being selected from a group consisting of copper, brass and iron, and said annular frame body is made of lead.

4. The tablet sample preparer in accordance with claim 3, wherein said annular frame body is fixed onto said substrate by soldering or spot welding.

5. The tablet sample preparer in accordance with claim 4, wherein said substrate is made of copper, and said annular frame body is made of lead.

6. The tablet sample preparer in accordance with claim 1, wherein said annular frame body is mounted on one end of said substrate, and said substrate is provided on its another end with an engage portion projecting toward a side being opposite to that provided with said frame body, said engage portion engaging with a sample holder of an infrared spectrophotometer for measuring said tablet sample thereby mounting said tablet sample on said infrared spectrophotometer.

* * * * *